United States Patent [19]

Stokowski et al.

[11] 4,390,708

[45] Jun. 28, 1983

[54] PROCESS FOR PRODUCING OXALYL CHLORIDE AND INTERMEDIATES

[75] Inventors: Robert J. Stokowski; Gerard Tertzakian, both of Edmonton; Tomoki C. S. Ruo, Calgary, all of Canada

[73] Assignee: Terochem Laboratories Ltd., Edmonton, Canada

[21] Appl. No.: 236,789

[22] Filed: Feb. 23, 1981

[51] Int. Cl.³ .......................................... C07D 317/42
[52] U.S. Cl. ................................................... 549/229
[58] Field of Search ...................... 260/340.2; 549/229

[56] References Cited

U.S. PATENT DOCUMENTS 2,816,287  12/1957  Ellingboe et al. ................... 260/463
3,313,719  4/1967   Springmann et al. ............. 260/340.2

FOREIGN PATENT DOCUMENTS 602104  7/1960  Canada ............................ 260/340.2
778734  7/1957  United Kingdom ............. 260/340.2

*Primary Examiner*—Ethel G. Love
*Attorney, Agent, or Firm*—Ernest P. Johnson

[57] ABSTRACT

A process is provided for producing oxalyl chloride by first photochemically chlorinating ethylene carbonate to form tetrachloroethylene carbonate and hydrogen chloride and then decomposing the tetrachloroethylene carbonate to oxalyl chloride and phosgene. The chlorination reaction is performed in a reaction vessel having an illuminated side arm conduit of narrow cross-sectional area. Chlorine is introduced at the base of the conduit and together with the hydrogen chloride evolved in the reaction continuously circulates the ethylene carbonate-chlorine reaction mixture through the narrow reaction zone within the conduit. The temperature of the ethylene carbonate-chlorine reaction mixture is controlled in the range of 70° to 100° C., preferably in the range of 79° to 81° C. The tetrachloroethylene carbonate is decomposed by heating same with a catalytic amount of a tertiary amine or amide.

10 Claims, 4 Drawing Figures

PROCESS FOR PRODUCING OXALYL CHLORIDE AND INTERMEDIATES

BACKGROUND OF THE INVENTION

1. Field of the Invention

The present invention relates to a process for chlorinating ethylene carbonate to produce tetrachloroethylene carbonate. The latter is decomposed to produce oxalyl chloride and phosgene.

2. Background Information

Oxalyl chloride $(COCl)_2$ is a useful reagent, for example as a chlorinating agent, in a large number of processes in the chemical and agricultural industries. Heretofore, oxalyl chloride has most often been produced by a solid phase reaction between phosphorous pentachloride and oxalic acid according to the equation:

$$(COOH)_2 + 2PCl_5 \rightarrow (COCl)_2 + 2POCl_3 + 2HCl.$$

This reaction is difficult to control, as it is a solid-solid reaction and involves both endothermic and exothermic stages. The yields of oxalyl chloride are unpredictable and usually very low, in the order of 30–50%. Further, greater than stoichometric quantities of phosphorous oxychloride are produced. This by-product is hazardous and, unless produced in very large amounts, represents a difficult waste product to dispose of or store.

Another process for producing oxalyl chloride is disclosed in U.S. Pat. No. 2,816,287 issued Dec. 10, 1957, and assigned to E. I. duPont de Nemours and Company. The process involves photochemically chlorinating ethylene carbonate (I) to form the tetrachloro derivative (II) and subsequently decomposing the tetrachloroethylene carbonate (II) to oxalyl chloride (III) and phosgene gas (IV) as represented by the following equations:

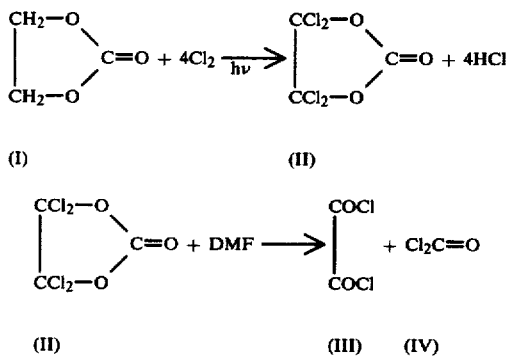

Under the conditions set forth in the duPont patent, the above process, in the inventors' experience, gives unpredictable by-products and low yields in both the chlorination and decomposition stages. Also, in scaling up the process from the bench top examples given in the duPont patent, to a commercial scale, the inventors needed to overcome many unpredictable problems.

More particularly, the duPont patent teaches chlorinating ethylene carbonate by bubbling chlorine into a refluxing mixture of ethylene carbonate and carbon tetrachloride in an illuminated flask equipped with a stirrer. The carbon tetrachloride is included in a very large amount, and thus controls the reflux temperature of the above reaction to about 75°–85° C. The reaction is judged to be complete when the yellow color of free chlorine persists for 30 minutes after cessation of chlorine addition. The tetrachloroethylene carbonate product is fractionated from the carbon tetrachloride solvent.

A number of problems are associated with the use of such a large excess of the carbon tetrachloride solvent. The solvent cuts down on the productivity of a given reaction vessel, reduces the light penetration, increases the reaction time and increases the overall costs of the process. Further, the tetrachloroethylene carbonate product must be fractionated from the solvent at the end of the reaction before proceeding to the decomposition step.

Another problem with the above process concerns the use of mechanical stirrers. The corrosive nature of the chemicals involved is sufficient to corrode metal and even teflon coated stirring devices.

Further, in scaling up this photochemical chlorination process to a commercial scale, it is difficult to achieve good light penetration. As the size of a flask-type reaction vessel is increased, the ratio of surface area to volume decreases. Thus light transmission is reduced, and the reaction time is increased. The duPont reference gives no information concerning a large scale operation of their process.

In French Pat. No. 1,363,740, issued May 4, 1964, and assigned to Chemische Werke Huls Aktiengesellschaft, a process is disclosed for preparing tetrachloroethylene carbonate wherein ethylene carbonate is photochemically chlorinated in the absence of a solvent. While the above patented process overcomes the problems associated with the use of a large excess of solvent, it does not confront the problems of stirring and illuminating the reaction mixture on a large scale.

SUMMARY OF THE INVENTION

In accordance with one broad aspect of the present invention, the chlorination of ethylene carbonate to tetrachloroethylene carbonate is improved. Ethylene carbonate is contacted with chlorine in a reaction vessel at a temperature in the range of 70°–100° C. The reaction mixture is continuously circulated through an illuminated reaction zone of narrow cross-sectional area and back into the reaction vessel to form tetrachloroethylene carbonate and hydrogen chloride. Preferably, the narrow reaction zone comprises a side arm connected at its upper and lower ends to the reaction vessel, and the chlorine gas is introduced at the lower end of the side arm. This arrangement enables the chlorine gas, together with the hydrogen chloride evolved in the reaction, to circulate the reaction mixture without the use of mechanical stirrers. Furthermore the provision of the narrow illuminated reaction zone overcomes the problems of light penetration in a large reaction vessel.

To produce oxalyl chloride, the tetrachloroethylene carbonate is decomposed by heating same with a catalytic amount of a tertiary amine or amide to yield oxalyl chloride and phosgene gas. Conventional gas-liquid separation techniques are used to separate the phosgene and oxalyl chloride. Dimethylformamide is the preferred catalyst for the decomposition reaction.

The inventors have found temperature to be an important parameter to control in the chlorination reaction. The temperature of the reaction mixture is preferably controlled in the range of about 70°–100° C. Below 70° C., the chlorination proceeds too slowly, and above 85° C., solid by-products begin to form which reduce light transmission and yields. Above 100° C. these problems significantly impair the reaction. More preferably, the reaction temperature is controlled in the range of about 72°-77° C. during the initial chlorination reaction. Once the reaction rate slows down, indicating that the dichloro derivative has been formed, the reaction temperature is preferably controlled in the range of about 79°-81° C.

The inventors have also found that, while the chlorination reaction proceeds in the absence of carbon tetrachloride, a small amount of an initiator, either carbon tetrachloride or tetrachloroethylene carbonate, preferably should be included to aid in the reaction. This reduction in, or elimination of, the solvent overcomes or reduces the above described problems associated with excessive amounts of solvent. Also, the tetrachloroethylene carbonate produced by this preferred embodiment of the invention, does not need to be fractionated before proceeding to the decomposition reaction.

Broadly stated, the invention is a process for producing oxalyl chloride comprising: contacting ethylene carbonate with chlorine in a reaction vessel at a temperature in the range of about 70° to 100° C.; continuously circulating the above reaction mixture from the reaction vessel through an illuminated reaction zone of reduced cross-sectional area relative to that of the reaction vessel, and back into the reaction vessel to form tetrachloroethylene carbonate and hydrogen chloride; venting the hydrogen chloride from the reaction vessel; decomposing the tetrachloroethylene carbonate by heating tetrachloroethylene carbonate with a catalytic amount of a tertiary amine or amide to form oxalyl chloride and phosgene gas; and separating the phosgene gas from the oxalyl chloride.

The invention also broadly provides a process for producing tetrachloroethylene carbonate, comprising: contacting ethylene carbonate with chlorine in a reaction vessel at a temperature in the range of about 70° to 100° C.; continuously circulating the above reaction mixture from the reaction vessel through an illuminated reaction zone of reduced cross-sectional area relative to that of the reaction vessel, back into the reaction vessel to form tetrachloroethylene carbonate and hydrogen chloride; and adding the chlorine to the reaction zone such that the added chlorine, together with the hydrogen chloride evolved in the reaction zone, provides the drive for circulating the reaction mixture; and venting the hydrogen chloride from the reaction vessel.

DESCRIPTION OF THE PREFERRED EMBODIMENT

The process for producing oxalyl chloride takes place in two stages: firstly a chlorination reaction and secondly a decomposition reaction.

Figure 2:
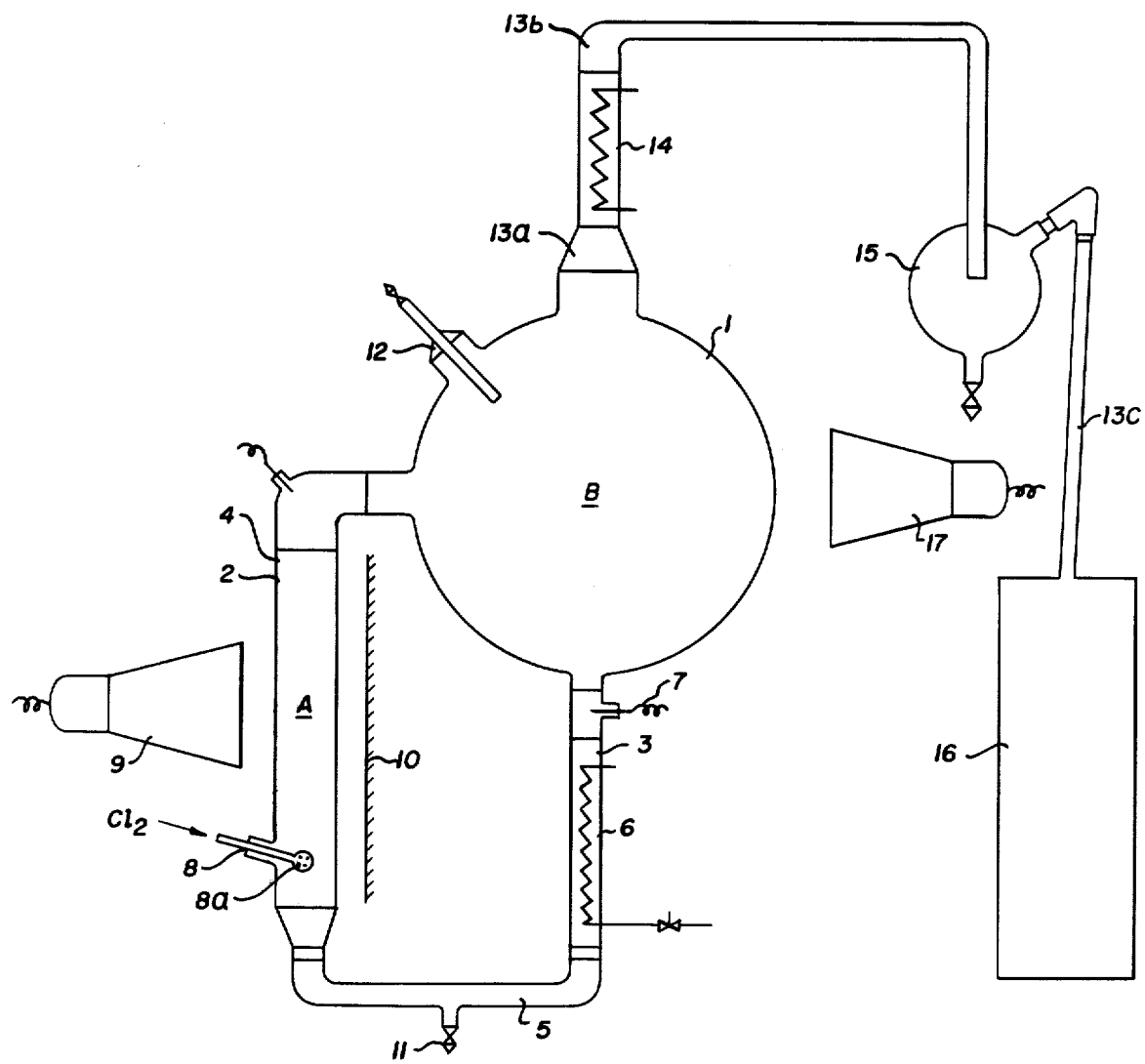
FIG. 2 is a schematic showing one form of the apparatus for conducting the chlorination step of the process to form tetrachloroethylene carbonate.

The chlorination reaction may be carried out in the apparatus shown in FIG. 2.

Such apparatus includes a reaction vessel 1 having a generally U-shaped side arm conduit 2 in communication therewith. The side arm conduit 2 has a vertical outlet leg member 3, leading downwardly from the base of the vessel 1, a vertical return leg member 4, leading upwardly back into the vessel 1, and a connecting leg member 5 which connects the two members 3 and 4.

A glass coil heat exchanger 6 is mounted in the outlet leg member 3. Hot or cold water may be circulated through the exchanger 6 to alter the temperature of the stream passing it. A thermowell 7 is mounted between the vessel 1 and the heat exchanger 6. The amount of heat or coolant introduced through the heat exchanger 6 is controlled in response to the temperature of the stream passing the thermowell 7.

The return leg member 4 forms a reaction zone A. It is to be noted that the cross-sectional area of the reaction zone A is reduced relative to the cross-sectional area of the vessel 1.

A chlorine gas inlet 8 is provided at the base of the return leg member 4. Chlorine is introduced from a source not shown through a sparger 8a mounted in the inlet 8.

A clear mercury vapor lamp 9 is provided to illuminate the reaction zone A. To concentrate the light in the zone A, the return leg member 4 is surrounded with mirrors 10.

A run-off valve 11 is provided in the connecting leg member 5, for draining the vessel 1.

Turning now to the reaction vessel 1, it is provided with a sealed inlet 12, through which ethylene carbonate may be introduced. An overhead line 13a leads from the vessel 1. This line 13a connects with a reflux condenser 14, for demisting gases leaving the vessel 1. A line 13b connects the condensor 14 with a vapor trap 15, for collecting condensed vapors. The trap 15 also aids in detecting excess chlorine gas, as will be discussed later. A line 13c connects the trap 15 with a caustic scrubbing tower 16, for neutralizing the hydrogen chloride gas produced in the system, although this gas can be collected as a by-product if desired. A clear mercury vapor lamp 17 is provided to illuminate the reaction zone B in the vessel 1. While not shown, the vessel 1 is insulated with aluminum foil-backed fiberglass insulation.

Chlorine resistant glass with teflon gaskets is used in the above apparatus. QVF* process glass (*trade mark of Corning Process Systems, Corning Ltd., Stone, Staffordshire, England) is suitable for this purpose.

From the foregoing, it will be noted that the reaction mixture is heated to optimum temperature by the heat exchanger 6 just before entering the reaction zone. A. The introduction of the chlorine gas into the base of the return leg member 4 and the evolution of large amounts of hydrogen chloride gas combine to cause self-circulation of the reaction mixture, thereby eliminating the problems associated with corrosion of a stirrer or a recycle pump. Finally, the provision of a narrow, well illuminated reaction zone A coupled with introduction of the chlorine at the base of the zone A results in improved reaction efficiency.

In the chlorination process, a small amount (5-10% by weight) of carbon tetrachloride or tetrachloroethylene carbonate is preferably added to the reaction vessel 1 to act as an initiator. The inventors have found that chlorination will occur without an initiator, provided the initial temperature of the ethylene carbonate is greater than about 70° C. Molten ethylene carbonate, preferably at 65°–70° C., is then added through inlet 12. The lamps 9, 17, are then turned on to aid in heating the mixture to about 70° C. The chlorine gas is introduced in the side arm conduit 2, and circulation is effected.

The initial chlorination to the monochloro and dichloro derivatives proceeds readily above 70° C., the rate being limited by the rate of chlorine addition. It is preferable to control the temperature of the initial chlorination reaction at about 72°–77° C., to avoid production of undesirable solid by-products. The initial reaction is also exothermic and thus heats up the reaction mixture. The heat exchanger 6 is adjusted to cool the reaction mixture to less than about 100° C., and most preferably to about 72°–77° C.

During the chlorination reaction, large amounts of hydrogen chloride gas are produced. This gas evolution aids the chlorine in effecting circulation through the side arm conduit 2. The hydrogen chloride gas escapes through the condensor 14, and is neutralized in the caustic scrubbing tower 16. Any carbon tetrachloride in the reaction mixture readily vaporizes and is condensed and collected in the trap 15. The hydrogen chloride gas and carbon tetrachloride vapors leaving the reaction vessel 1 are contaminated with small amounts of reacted and unreacted ethylene carbonate. The gas and vapor stream is demisted by the condensor 14 to limit product loss.

The entire chlorination reaction takes several days to complete, the reaction time depending on the reaction scale, the temperature of reaction and the intensity of the mercury vapor lamps 9, 17. The reaction rate decreases considerably once dichloroethylene carbonate is formed. Chlorination from the dichloro derivative to the tetrachloro product is slow. The rate of chlorine gas addition can be reduced significantly during this stage of the reaction. Excess chlorine is easily detected by a yellow color in both the reaction mixture and the trap 15. Once this excess of chlorine is detected, the rate of the chlorine addition is reduced and the reaction temperature is preferably raised and controlled in the range of about 79°–81° C. The reaction will proceed in the temperature range of about 70°–100° C., however, below 70° C. the reaction rate is very slow, and above about 100° C., solid by-products form inhibiting light penetration and decreasing yields.

The reaction progress is easily followed by gas chromatographic analysis of the reaction mixture. It is important to take the reaction to completion to form substantially pure tetrachloroethylene carbonate. This enables the subsequent decomposition reaction to proceed smoothly without needing to first purify the tetrachloroethylene carbonate. With careful control of the abovedescribed reaction conditions in the chlorination process, this can be achieved.

The tetrachloroethylene carbonate thus formed is decomposed to oxalyl chloride and phosgene by heating the tetrachloroethylene carbonate with a catalytic amount of tertiary amine or tertiary amide. The oxalyl chloride is thereafter separated from the phosgene gas by a conventional gas-liquid separation technique.

Figure 3:
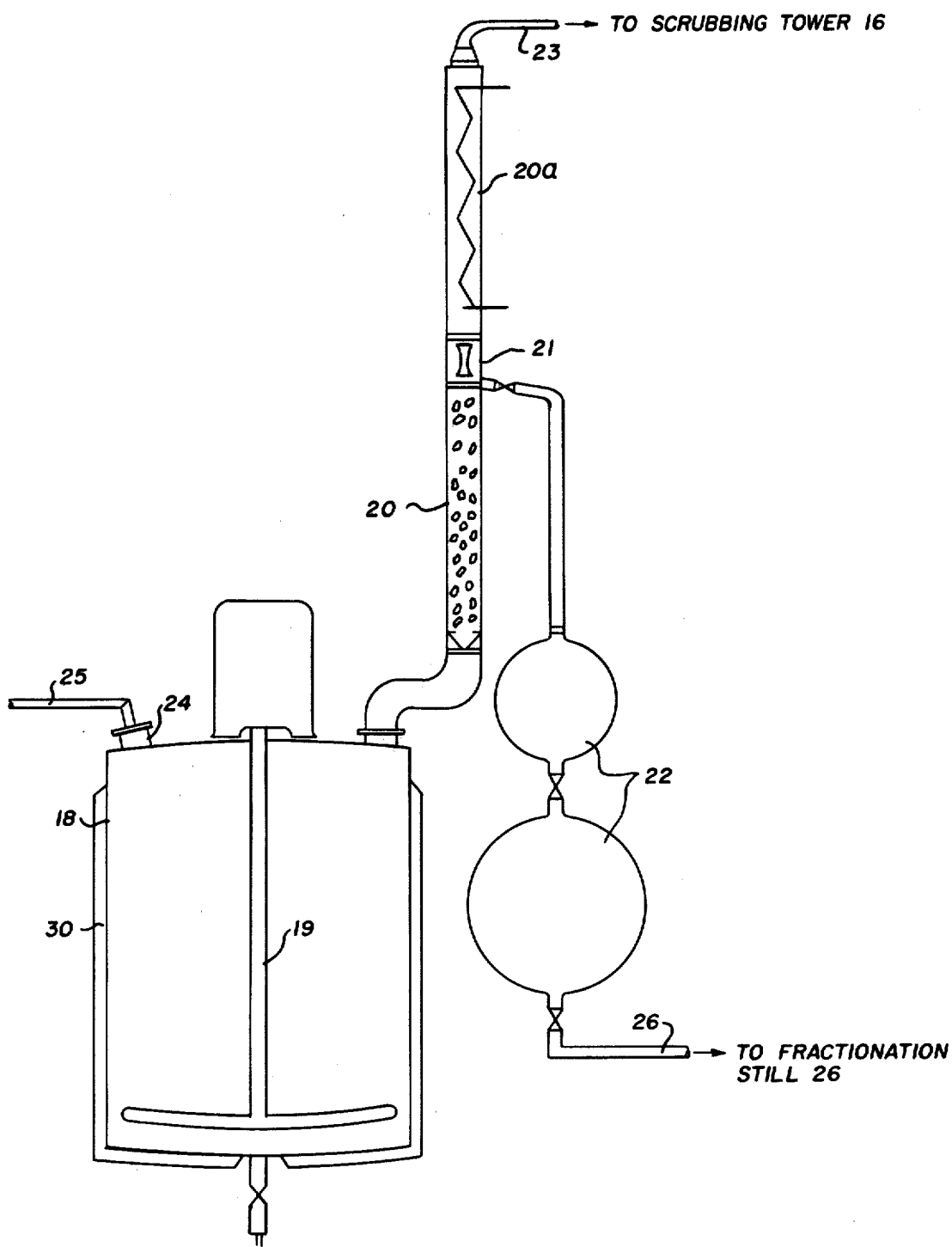
FIG. 3 is a schematic showing one form of the apparatus for decomposing the tetrachloroethylene carbonate.
Figure 4:
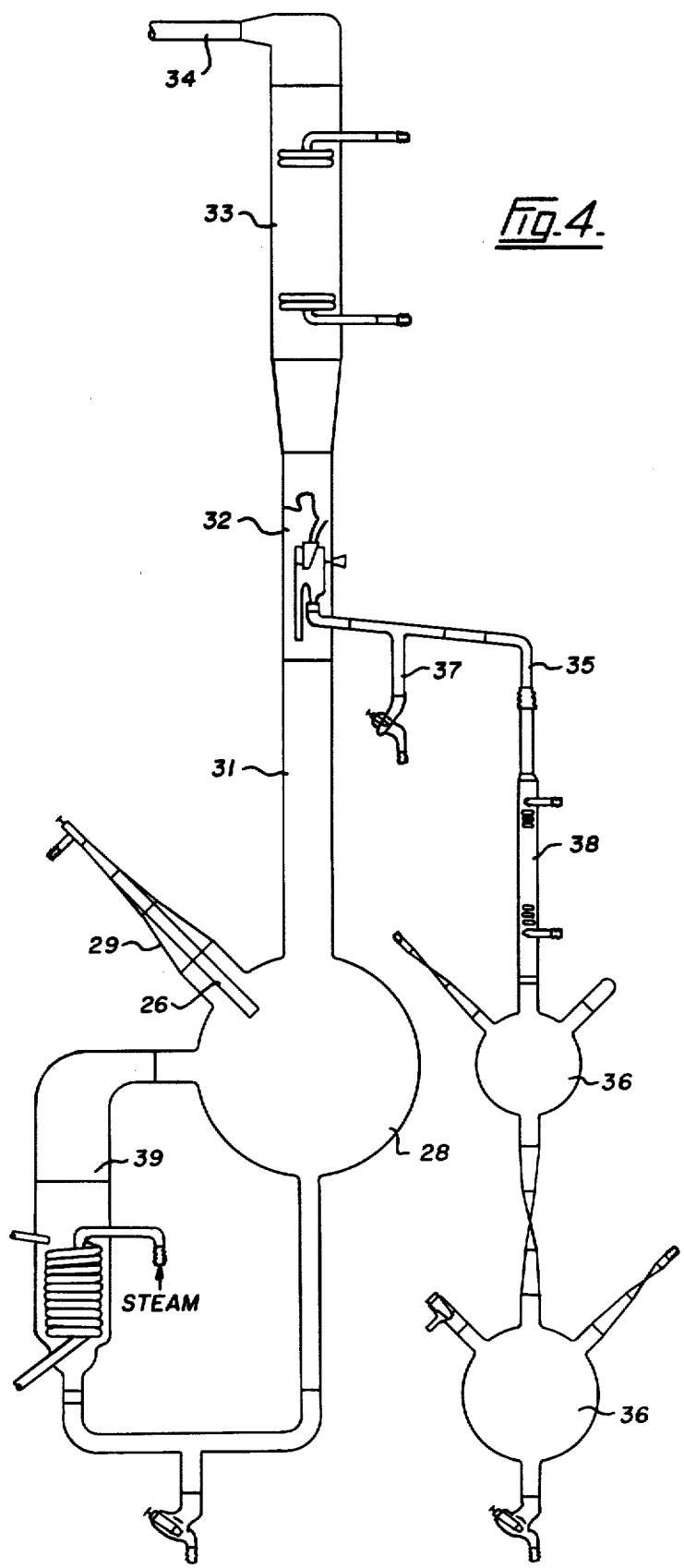
FIG. 4 is a schematic showing one form of the apparatus for the gas-liquid separation of the oxalyl chloride-phosgene mixture.

Embodiments of the apparatus for the decomposition and separation steps are shown schematically in FIGS. 3 and 4 respectively. The decomposition apparatus includes a closed reactor 18 having a mechanical stirring means 19. The reactor 18 is equipped for rough fractionation with an overhead glass packed column 20 and an overhead heat exchanger 20a. A reflux divider 21 is provided between the column 20 and the heat exchanger 20a to setting the reflux ratio. The reflux divider is in turn connected to collecting flasks 22 for collecting the crude oxalyl chloride-phosgene mixture. The upper end of the column 20 is connected through a line 23 to the caustic scrubbing tower 16 for destroying phosgene gas. The reactor 18 is provided with a sealed inlet 24 for introducing the tetrachloroethylene carbonate. A line 25 leads from the run-off valve 11 of the chlorination vessel 1 to the inlet 24. The reactor 18 is heated by a heating jacket 30. The collecting flasks 22 are connected through a line 26 to the gas-liquid separation apparatus shown in FIG. 4.

The gas-liquid separation apparatus shown is a conventional thermosyphon distillation apparatus of 200 liter capacity. It should be understood that other embodiments of this apparatus are available which are specifically designed for gas-liquid separation of two volatile components. The present embodiment, being readily available to the inventors, is however sufficient to illustrate the invention.

The distillation apparatus includes a flask 28 equipped with a sealed inlet 29. The line 26 from the decomposition apparatus is connected to this inlet 29. The flask 28 is also provided with an overhead fractionating column 31, which in turn includes a reflux divider 32 and a condensor 33. The upper end of the column 31 is connected through line 34 to the caustic scrubbing tower 16 for destroying the phosgene gas. The reflux divider 32 is connected through a line 35 to collecting flasks 36 for collecting the fractionated oxalyl chloride. The line 35 includes a vapour trap 37 and a condensor 38. The flask 28 is heated by a steam thermosyphon 39.

Chlorine resistant glass is used in both the decomposition apparatus and the gas-liquid separation apparatus.

In the decomposition reaction, tetrachloroethylene carbonate is introduced in the reactor 18 with a catalytic amount of a tertiary amine or amide. Dimethylformamide, in an amount of about 1% by weight, is the preferred catalyst. At room temperature dimethylformamide does not promote any appreciable decomposition. To initiate decomposition the mixture is heated to about 60° C. Thereafter, the rate of decomposition is limited by reducing the temperature to slightly less than 60° C. At the end of the reaction the temperature is raised well above the boiling point of oxalyl chloride to remove all of the oxalyl chloride from the reactor 18. Oxalyl chloride vapors and phosgene gas evolve simultaneously during the decomposition reaction and are collected in collecting flasks 22. A portion of the phosgene gas is allowed to escape through line 23 to the caustic scrubbing tower, thereby effecting a partial separation of the oxalyl chloride-phosgene mixture.

The collected oxalyl chloride-phosgene mixture is transferred to the fractionating still 28. The mixture is refluxed gently for several hours to remove the phosgene, and thereafter fractionated to yield an oxalyl chloride fraction of the desired purity.

The invention is further illustrated in the following example.

EXAMPLE

Figure 1:
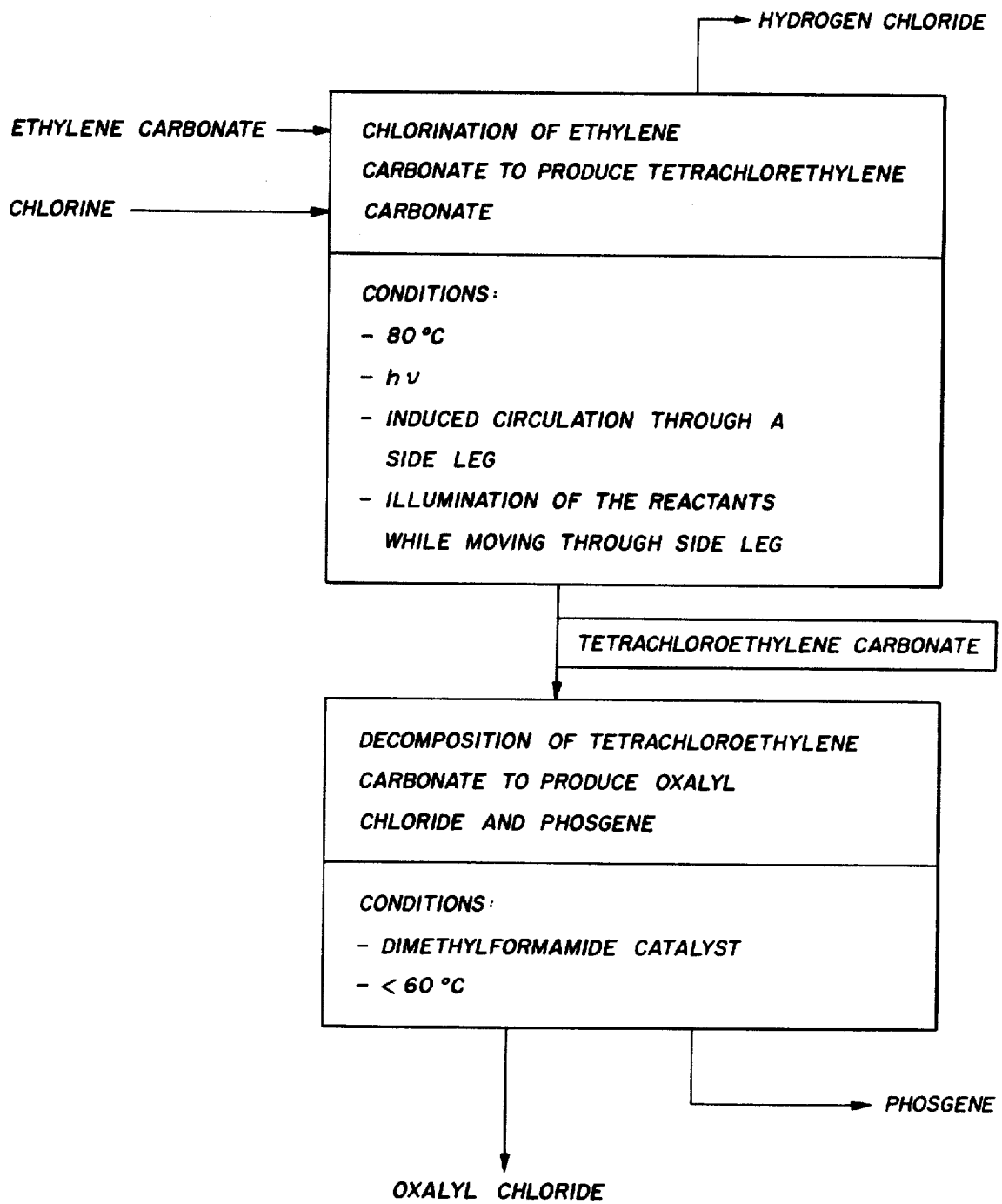
FIG. 1 is a block diagram showing the steps of the process.

The chlorination reaction shown in FIG. 1 was constructed using a 100 l. vessel 1 equipped with a 3" i.d. side arm conduit 2. QVF process glass and teflon gaskets were used throughout the vessel 1. The vertical return leg member 4 and the vessel 1 were each illuminated with 1000 watt clear mercury vapor lamps 9, 17, emitting light of wave lengths 430, 550, 575 nm. The heat exchanger 6 was set at 80° C.

Three to four liters of carbon tetrachloride were introduced in the vessel 1, followed by 88 kg of molten ethylene carbonate at about 70° C. Chlorine was supplied from 4-150 lb. net cylinders at their maximum rate to effect circulation.

Within 2-3 minutes the reaction was proceeding at its maximum rate. The mixture was controlled at 72° C. during this initial rapid stage of the chlorination reaction. Once the reaction rate had slowed, as evidenced by a light yellow color of excess chlorine, the temperature was increased and controlled at 80° C. for the duration of the reaction. Hydrogen chloride gas was vigorously evolved from the mixture and aided in the circulation. The gas was demisted in the overhead condensor 14, and was destroyed in a caustic scrubbing tower 16. The carbon tetrachloride vaporized and was collected in the trap 15.

The abovementioned excess of chlorine was detected after about 3 days by the presence of yellow gas in the trap 15. The reaction rate had slowed down considerably by this time. The rate of chlorine addition was reduced to about half its original rate, to maintain only a trace excess of chlorine in the reaction mixture as detected by a light yellow color in the mixture.

The entire reaction took 5-6 days to complete. During the latter stages of the reaction, the reaction mixture was analyzed by gas chromatographic analysis. At completion, the reaction mixture showed one smooth peak for tetrachloroethylene carbonate and less than 5% low boiling impurities. The yield of the tetrachloroethylene was calculated to be 91%.

The tetrachloroethylene carbonate was drained from the vessel 1 through the run off valve 11, leaving a residue of the product behind to act as an initiator for subsequent chlorination reactions. After about 4 chlorinations of 88 kg of ethylene carbonate, the reaction vessel 1 was washed with dilute caustic and rinsed with dilute HCl to remove any solid impurities on the vessel walls which would inhibit light transmission.

To decompose the tetrachloroethylene carbonate, 180 l. of the product were transferred to a 50 gal. Pfaudler* glass lined reactor 18 (*trade name of Pfaudler Co., Rochester, N.Y.) equipped for rough fractionation. About 1% by weight dimethylformamide was added to promote the decomposition. The mixture was heated to about 60° C. to initiate decomposition. Thereafter the temperature was held below 60° C. to limit the rate of decomposition. The temperature was increased to 80°-85° C. at the end of the reaction to ensure that all the oxalyl chloride was driven from the reactor 18. The decomposition took about 4 hours.

Oxalyl chloride vapors and phosgene gas were produced simultaneously from the reaction. A portion of the phosgene was removed by the rough fractionation equipment. The remaining oxalyl chloride-phosgene mixture was collected and transferred to a QVF fractionating still 28 for total phosgene removal. The mixture was refluxed slowly for 18 hours to remove the phosgene. The phosgene was destroyed in the caustic scrubbing tower 16. The remaining oxalyl chloride was fractionated, taking off an intermediate fraction boiling over 63°-65° C. as the product. The higher and lower boiling fractions were retained and refractionated. The yield of oxalyl chloride from the tetrachloroethylene was calculated to be 79%. It is anticipated that the yields for this last step could be increased with the use of equipment specifically designed for the gas-liquid separation of two volatile gas and liquid components.

While the present invention has been disclosed in connection with the preferred embodiment thereof, it should be understood that there may be other embodiments which fall within the spirit and scope of the invention as defined by the following claims.

The embodiments of the invention in which an exclusive property or privilege is claimed are defined as follows:

1. A process for producing tetrachloroethylene carbonate, comprising:
   contacting ethylene carbonate with chlorine in a reaction vessel at a temperature in the range of about 70° to 100° C.;
   continuously circulating the above reaction mixture from the reaction vessel through an illuminated reaction zone of reduced cross-sectional area relative to that of the reaction vessel to form tetrachloroethylene carbonate and hydrogen chloride;
   adding the chlorine at the reaction zone, such that the added chlorine, together with the hydrogen chloride evolved in the reaction zone, provides the drive for circulating the reaction mixture; and
   venting the hydrogen chloride from the reaction vessel.

2. The process as set forth in claim 1, which further comprises:
   providing an initiator, selected from the group consisting of carbon tetrachloride and tetrachloroethylene carbonate, in contact with the reaction mixture.

3. The process as set forth in claim 1, wherein:
   the temperature of the chlorination reaction is controlled in the range of about 72°-77° C. until the reaction rate decreases, and is then controlled in the range of about 79°-81° C. for the duration of the reaction.

4. The process as set forth in claim 1, wherein:
   the temperature of the chlorination reaction is controlled in the range of about 72°-77° C. until the reaction rate decreases, and is then controlled in the range of about 79°-81° C. for the duration of the reaction.

5. The process as set forth in claims 1, 3 or 4 which further includes:
   illuminating the reaction vessel.

6. A process for producing tetrachloroethylene carbonate, comprising:
   contacting ethylene carbonate with chlorine in a reaction vessel;
   continuously circulating the above reaction mixture from the reaction vessel through a generally U-shaped side arm conduit of reduced cross-sectional area relative to that of the reaction vessel and back into the reaction vessel to form tetrachloroethylene carbonate and hydrogen chloride, said side conduit including a downwardly extending leg leading from the base of the reaction vessel, and an upwardly extending leg leading from the downward leg back to the reaction vessel;
   adding the chlorine at the lower end of the reaction zone, whereby the chlorine together with the hydrogen chloride evolved in the reaction provides the drive for circulating the reaction mixture;
   controlling the temperature of the reaction mixture in the side arm conduit, before the reaction mixture enters the reaction zone, in the range of about 70° to 100° C.; and venting the hydrogen chloride from the reaction vessel.

7. The process as set forth in claim 6, wherein:

the temperature of the reaction mixture in the side arm conduit, before entering the reaction zone, is controlled in the range of about 72°-77° C. until the reaction rate decreases, and is then controlled in the range of about 79°-81° C. for the duration of the reaction.

8. The process as set forth in claim 7, which further comprises:

providing an initiator, selected from the group consisting of carbon tetrachloride and tetrachloroethylene carbonate, in contact with the reaction mixture.

9. The process as set forth in claim 6, 7 or 8, which further comprises:

illuminating the reaction vessel.

10. The process as set forth in claim 1, which further comprises:

controlling the temperature of the reaction mixture in the reaction zone, by adjusting the temperature of the reaction mixture before it enters the reaction zone, in the range of about 70° to 100° C.

* * * * *